United States Patent [19]
McGuire

[11] Patent Number: 6,155,831
[45] Date of Patent: *Dec. 5, 2000

[54] NON-SURGICALLY RETRIEVABLE GUIDED TISSUE REGENERATION MEMBRANE

[76] Inventor: Michael K. McGuire, 3400 S. Gessner, Suite 102, Houston, Tex. 77063

[*] Notice: This patent issued on a continued prosecution application filed under 37 CFR 1.53(d), and is subject to the twenty year patent term provisions of 35 U.S.C. 154(a)(2).

[21] Appl. No.: 09/261,644

[22] Filed: Mar. 3, 1999

[51] Int. Cl.⁷ ............................................... A61C 5/00
[52] U.S. Cl. ........................................... 433/215; 433/138
[58] Field of Search .................................... 433/136, 138, 433/140, 215; 606/151, 154, 155, 156; 424/426, 435, 444

[56] References Cited

U.S. PATENT DOCUMENTS

| | | | |
|---|---|---|---|
| 5,059,123 | 10/1991 | Jernberg | 433/215 |
| 5,093,179 | 3/1992 | Scoatlebury et al. | 433/215 X |
| 5,171,148 | 12/1992 | Wasserman | 433/215 |
| 5,197,882 | 3/1993 | Jernberg | 433/215 |
| 5,297,563 | 3/1994 | Syers | 128/898 |
| 5,360,341 | 11/1994 | Abromowitz | 433/215 |
| 5,511,565 | 4/1996 | Syers | 18/898 |
| 5,520,921 | 5/1996 | Chalifoux | 433/138 X |
| 5,607,689 | 3/1997 | Checchi | 424/435 |
| 5,899,694 | 5/1999 | Summer | 433/136 |

*Primary Examiner*—Nicholas D. Lucchesi
*Attorney, Agent, or Firm*—Mark R. Wisner

[57] ABSTRACT

A dental appliance consisting of a biocompatible, non-absorbable retrievable membrane material may be used as a separation and isolation barrier following periodontal surgery to promote tissue regeneration. The appliance is configured with a cord woven into the inferior aspect of the membrane and extends up from the apical border of the membrane through a loop in the superior border. The free end of the cord extends through the gingival sulcus and remains exposed while the membrane is in place. At the appropriate time for membrane removal, the sutures holding the membrane in place are released and the membrane removal cord is use to lift the membrane through the sulcus by gently pulling on the cord. The non-surgical removal of the membrane using this method reduces further surgical trauma to the patient and eliminates the risk that surgical removal of the membrane could damage the newly regenerated tissue.

4 Claims, 3 Drawing Sheets

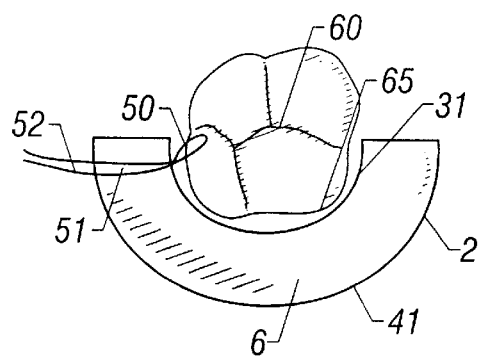
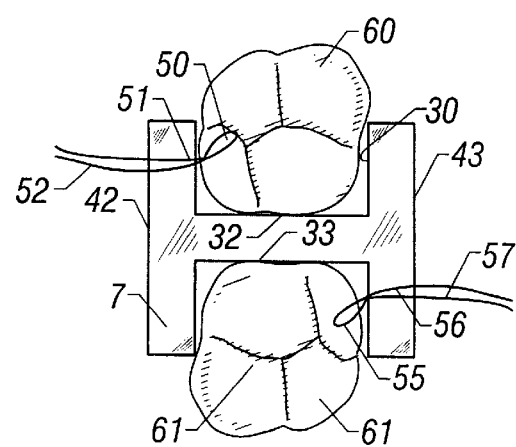
FIG. 5
FIG. 6
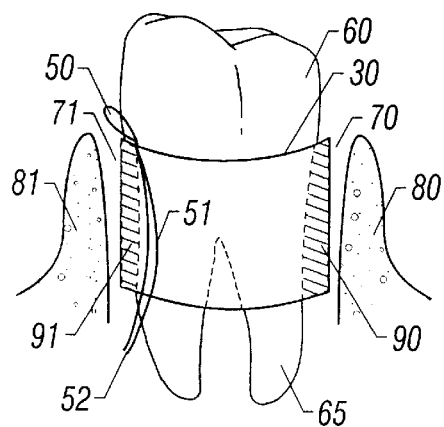
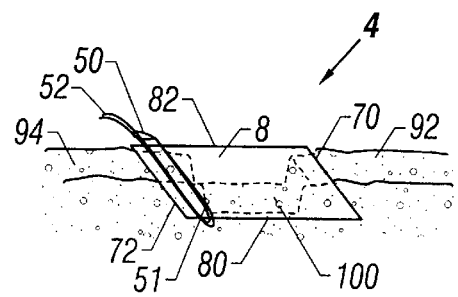
FIG. 7
FIG. 8

NON-SURGICALLY RETRIEVABLE GUIDED TISSUE REGENERATION MEMBRANE

BACKGROUND OF THE INVENTION

This invention relates to the field of oral surgery, and more specifically, periodontal surgery. The invention provides a method and appliance for promoting the healing of oral tissues including bone, which have been damaged by disease.

Periodontal disease occurs when bacteria (plaque) proliferate on the teeth and gums. If the bacteria are allowed to remain, they eventually cause inflammation of the gums and may destroy gum tissue. The condition worsens when the bacterial infection attacks the underlying bone. In many cases, the periodontal infection is advanced and some of the underlying bone will have been destroyed before the patient seeks treatment.

The body may regenerate bone tissue lost to periodontal disease. It is known in the art that the cell type that repopulates the root surface after periodontal surgery will determine the type of attachment that ultimately forms. Animal studies have shown showing different healing responses occurred when various periodontal tissues came into contact with the root surface.

More rapid regeneration of bone tissue may be promoted by isolating the bone from other proximate tissues and especially from the gum tissue overlying the bone. A physical barrier may be used to separate the bone tissue from the surrounding tissues and thus promote selective cell repopulation of the root surface in turn facilitating periodontal regeneration. A barrier may also be used to promote regeneration of other oral tissues, such as the cementum, a layer on the tooth, and the periodontal ligament, which joins the tooth to the bone. The barrier facilitates regeneration of the isolated tissue by preventing surrounding gum tissues from filling empty space formerly occupied by bone and or periodontal ligament. The invagination by gum tissue, if permitted, prevents the bone from restoring itself to its former condition and configuration. The barrier thus promotes the regeneration of the damaged bone, cementum, and periodontal ligament over the growth of other oral tissues, specifically gum tissue.

It has been demonstrated that a variety of membranes can be used to facilitate the regeneration of the periodontal attachment apparatus. The barrier accepted as the standard in the field is made of expanded polytetrafluoroethylene (ePTFE). The barrier is placed as part of the original periodontal surgical procedure.

The non-absorbable nature of the ePTFE membrane requires a second surgical procedure for removal of the barrier. This removal is usually scheduled 4–8 weeks after the insertion of the membrane, and is usually accomplished under local anesthetic. Surgical removal of the membrane poses potential risk to the newly regenerated tissue as well as surgical trauma to the patient. This risk and trauma may be eliminated by adoption of a non-surgical approach to membrane removal.

A variety of absorbable membranes have been developed which do not require removal. However, practitioners skilled in the art consider use of the ePTFE membrane most likely to yield the most optimal outcome for tissue regeneration. The instant invention provides a periodontal barrier incorporating a membrane retrieval device that will facilitate non-surgical removal of the non-absorbable barrier membrane.

Non-absorbable barriers have been shown to produce superior tissue regeneration and provide more durable and long lasting protection in covering blood clots. The invention reduces the need for extensive surgical removal of the barrier thus reducing (1) the risk to the newly regenerated tissue, (2) additional surgical trauma to the patient and (3) enables better utilization of the clinicians time.

DESCRIPTION OF THE PRIOR ART

U.S. Pat. No. 5,511,565 was issued Apr. 30, 1996 to Syers. No assignment was designated. This patent discloses a device and method for facilitation of guided tissue regeneration after occurrence of a bony deficit comprising a barrier to be placed over the deficit to protect the tissue and allow regeneration wherein said barrier includes an elongate member such as a cord to facilitate removal of the barrier by providing a convenient grasping point for the clinician (Col. 2, Line 16), (Col. 5, Line 11). The patent states that (Col. 1, Line 65) that the barrier may be formed of a resorbable material; alternatively, it can be nonresorbable and require subsequent surgical removal (Col. 1, Line 65). The patent further states that the elongate member is usually placed partially within a hollow structure dimensioned to accept the barrier. When traction is placed on the elongate member while the hollow structure is stabilized, the barrier is pulled into the hollow structure (Col. 2, Line 19), (Col. 5, Line 11). The patent further discloses incorporation of electrically conductive fibers into the membrane to facilitate transmission of galvanic current to the barrier. Claim 11 of the patent recites, in pertinent part, a barrier (membrane) including an attached cord and a tube dimensioned to accept the cord therethrough. The patent does not provide any description of where or how the elongate member is attached to the membrane, if or how the hollow structure is affixed in the tissue or minimal dimensions of the hollow needed to accommodate the barrier stiffened with the incorporated conducting wires.

U.S. Pat. No. 5,607,689, was issued Mar. 4, 1997 to Checchi and assigned to I Sugheri, s.r.l. This patent discloses a device for guiding tissue regeneration comprising a non-absorbable membrane insertable under the gingiva, said membrane being preformed according to established shapes that depend on the tooth size and shape. The patent does not disclose a means for extracting the membrane other than surgery.

U.S. Pat. No. 5,360,341 was issued Nov. 1, 1994 to Abromowitz. No assignment was noted. This patent discloses a device that promotes the healing of oral tissues destroyed by periodontal diseases. Tne device comprises a flat piece of elastic material connected at it opposing edges to two pieces of non-absorbable, biocompatible membrane, said elastic material having one or more punched holes which allow the material to be fitted around the patient's teeth thereby forming a protective barrier and promoting tissue regeneration. The patent does not disclose any easy means for extracting the membrane.

U.S. Pat. No. 5,297,563 was issued Mar. 29, 1994 to Syers. No assignment was noted. This patent discloses a device for facilitation of tissue and bone guided regeneration of a bony deficit comprising a non-resorbable barrier placed over a tissue deficit. The barrier must be surgically removed.

U.S. Pat. No. 5,197,882 was issued Mar. 30, 1993 to Jernberg and assigned to Gary R. Jernberg. This patent discloses a biocompatible, non-absorbable periodontal barrier and method for use in guided regeneration. The device comprises a membrane which houses chemotherapeutic agents for aiding and guiding tissue regeneration. The membrane must be surgically implanted and sutured into place.

The patent does not disclose a non-surgical method for extracting the membrane.

U.S. Pat. No. 5,059,123 was issued Oct. 22, 1991 to Jernberg. No assignment was noted. This patent discloses a non-absorbable periodontal barrier and method proving for sustained controlled delivery and enhanced uptake of microencapsulated, chemotherapeutic agents to a tissue regeneration site. The barrier must be surgically implanted and removed.

SUMMARY OF THE INVENTION

The instant invention provides a periodontal barrier incorporating a membrane retrieval device that facilitates non-surgical removal of the non-absorbable barrier membrane. The retrieval device consists of a doubled cord comprising a loop, a central portion and free ends. The central portion of the doubled cord is woven in or otherwise affixed to the inferior aspect of the barrier membrane. The loop formed by the doubled cord extends up from the superior border of the membrane. The free ends of the cord extend from the inferior border of the membrane. After the membrane is placed around or over the tissue or bone deficit, the free ends of the cord are drawn through the loop and are positioned to extend through the gingival sulcus. The free ends remain exposed while the membrane is in place. At the appropriate time for membrane removal, the sutures holding the membrane in place are released. The free ends of the membrane retrieval cord are grasped with a forceps and through gentle tension applied to the free ends of the cord, the inferior border of the membrane is retracted and the membrane rolls up upon itself moving occlusally. Ultimately, the entire membrane is pulled through the sulcus by maintaining tension on the cord.

The membrane retrieval cord largely eliminates the need for secondary surgery to remove the membrane. Even in those cases where surgical membrane removal is indicated, the cord provides a simpler and less invasive method for removal. The cord provides superior mechanical advantage for membrane retraction and eliminates the need for blind exploration by the clinician to identify a comer of the membrane, which can be grasped by forceps and used to remove the membrane. Using the cord, the membrane can be removed under only topical anesthetic in most instances.

BRIEF DESCRIPTION OF THE DRAWINGS

FIG. 5 is a top view illustrating a second preferred embodiment of a device constructed in accordance with the invention comprising a retrievable barrier membrane with a doubled cord affixed thereto. The view is taken from above the surface of the teeth looking down towards the biting/chewing surface of the tooth with the barrier membrane in proximity to the neck of the tooth. The barrier membrane extends radially outward from the tooth and lies circumferentially around the tooth and is shown before the barrier membrane is placed proximally to a tissue deficit.

FIG. 6 is a top view taken in the same manner as the view in FIG. 5 and illustrates a third preferred embodiment of a device constructed in accordance with the invention comprising a barrier membrane with a doubled cord affixed thereto. FIG. 6 is a view from above the surface of the teeth with a view down towards the biting/chewing surface of the teeth with the barrier membrane placed between two teeth.

FIG. 7 is a sectional view of gums and teeth illustrating additional details of the device in accordance with the invention. The retrievable barrier membrane is placed in proximity to a tooth. The sectional plane of FIG. 7 displays the roots of the tooth embedded in the bone of the jaw, the sulci between the bone and the tissue of the gum and the gums.

FIG. 8 is a perspective view illustrating a fourth preferred embodiment of a device in accordance with the invention. In FIG. 8, the retrievable barrier membrane is shown covering a tissue deficit.

In FIG. 10, the view is through the gum (not shown) of a retrievable barrier membrane with attached cord where the barrier membrane is covering a tissue deficit in a bony mass. The free ends of the retrieval cord are shown placed through the loop in the cord.

DETAILED DESCRIPTION OF THE PREFERRED EMBODIMENT

This invention provides devices and methods to facilitate non-surgical retrieval of a barrier membrane used to enhance tissue regeneration of a bony deficit. Further, the invention facilitates non-surgical retrieval of a barrier membrane used to protect a blood clot after a surgical procedure. By protecting and covering this blood clot, the barrier facilitates regeneration of the surrounding tissues. The invention reduces the need for extensive surgical procedures to remove the barrier. The ability to remove the barrier using the instant invention reduces the risk of ablation of the newly regenerated tissue, additional surgical trauma to the patient and enables better utilization of the clinician's time.

Figure 1:
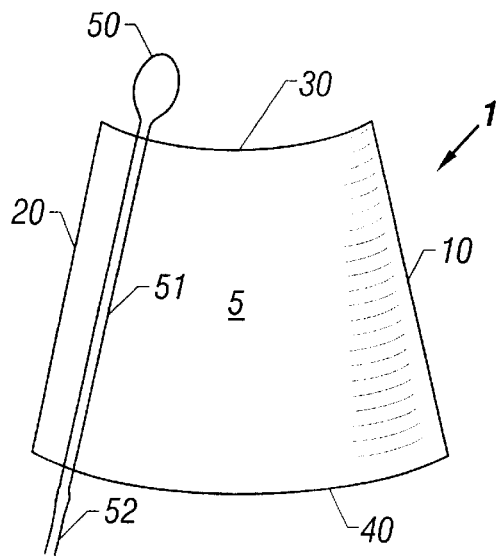
FIG. 1 is a side elevation view defining a device in accordance with the invention showing a retrievable barrier membrane with a cord affixed thereto. The cord is doubled to form a loop. The intermediate portions of the cords connect the loop to the two free ends of the cord. The intermediate portion of the doubled cord is affixed to or woven into the barrier membrane. The loop portion of the doubled cord extends from the superior side of the barrier membrane, and the free ends of the cord extend from the inferior side of the barrier membrane.

In the first preferred embodiment as shown in FIG. 1, the retrievable mechanical barrier 1 includes a barrier membrane 5, a retrieval device of a doubled cord comprising a loop 50, formed from the center portion of the doubled cord and extending from the superior border 30 of the membrane 5, an intermediate portion of the doubled cord 51 affixed to the membrane barrier 5, and the free ends of the cord 52 extending from the inferior border 40 of the barrier membrane 5. The mechanical barrier of FIG. 1 is further defined with a first lateral border 10 and a second lateral border 20. Alternative shapes of the barrier membrane are depicted in FIGS. 5, 6, 8 and 10. Each of the barrier membranes depicted in the figures is provided with one or more retrieval cords. Each cord is doubled with its central portion affixed to the membrane and running from the superior (occlusal) border to the inferior (periostal) border. A loop formed from the cord extends from the superior border. The free ends of the cord extend from the inferior border. After placing the barrier membrane in position over a bony deficit and suturing or attaching it in place, the free ends of the doubled cord are drawn through the loop extending from the superior border. The free ends of the cord are positioned to extend through the gingival sulcus and remain exposed while the membrane is in place. At the appropriate time for membrane removal, the sutures or other devices holding the membrane in place are released. The membrane retrieval cord free ends are grasped with a forceps and through gentle tension applied to the free ends, the inferior border of the membrane is retracted and the membrane rolls up upon itself. Ultimately, the entire membrane is pulled through the sulcus and removed by maintaining tension on the free ends of the cord. The following description of the preferred embodiments augments and expands the detailed description of the instant invention.

Figure 2:
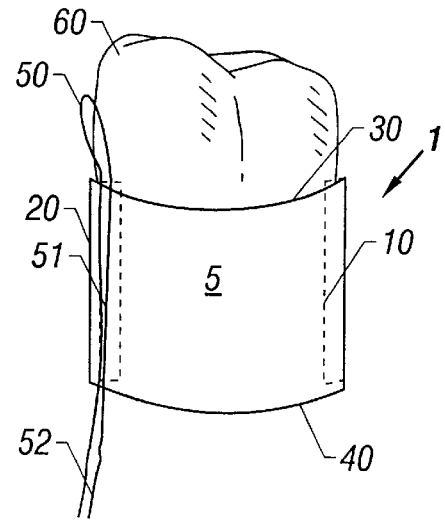
FIG. 2 is a schematic side view showing the retrievable barrier membrane constructed in accordance with the invention in place proximate to a tooth. The superior side of the barrier membrane is always placed in closest proximity to the surface of the tooth or teeth adjacent to the placement of the barrier membrane. The inferior side of the barrier membrane is always placed furthest away from the tooth or teeth surface(s) adjacent to the membrane barrier position.

The first preferred embodiment is further illustrated in FIG. 2 which displays a schematic side view (either mesial or distal view ) of a tooth 60 with the retrievable membrane barrier 1 in proximity. In FIG. 2, the free ends 52 of the retrieval cord have not been drawn through the loop 50.

Figure 3:
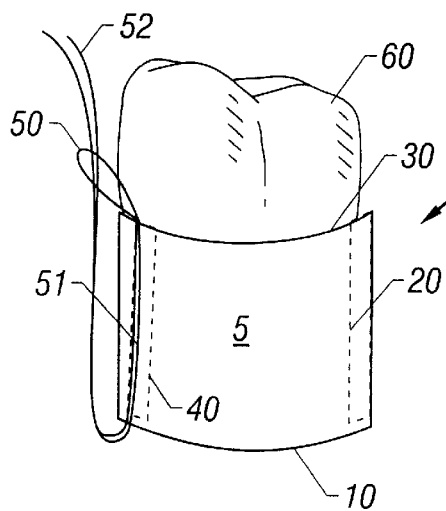
FIG. 3 is a schematic side view of the retrievable barrier membrane of FIG. 2 further showing placement of the barrier membrane in proximity to a tooth. In this instance, as in FIG. 2, the loop of the doubled cord is shown extending from the superior border of the membrane. The view in both FIG. 2 and Figure shows either the mesial or distal aspect of the tooth displayed. The loop would be on the lingual or facial side of the tooth. The free ends of the cord are shown inserted through the loop.

FIG. 3 illustrates the retrievable membrane barrier 1 of FIGS. 2 and 3 but with the free ends 52 of the retrieval cord drawn through the loop 50.

Figure 4:
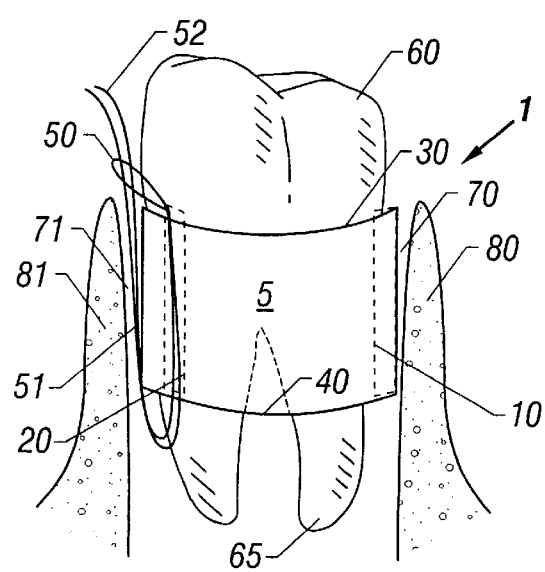
FIG. 4 is a schematic side view of the retrievable barrier membrane of FIGS. 1 and 2 further showing placement of the barrier membrane. The free ends of the cord extending from the inferior border to the superior border are shown inserted through the loop with the loop and the free ends of the cord extending from the sulcus in which the portion of the barrier membrane to which the doubled cord is affixed has been situated. The sulcus is the space between the inner portion of the gum and the bone holding the roots of the tooth.

FIG. 4 illustrates the first preferred embodiment of the retrievable barrier membrane 1 with retrieval cord comprising loop 50, intermediate portion 51 affixed to the barrier membrane 5, and free ends 52 drawn through loop 50. Both free ends 52 and loop 50 extend from the superior border of the barrier membrane 5. The retrievable barrier membrane 1 is proximal to a tooth 60 with roots 65. FIG. 4 further illustrates the location of the intermediate portion 51 of the retrieval cord in the ginvigal sulcus 71 separating the bony tissue in which the tooth 60 is embedded from the gum tissue 81. Following the description of use of the invention above, after placing the retrievable barrier membrane 1 in position over a bony deficit or blood clot and suturing it or attaching it in place, the free ends 52 of the doubled cord are drawn similarly through the loop 50 so that both the loop 50 and the free ends 52 extend from the superior border 30. The free ends of the cord 52 are positioned to extend through the gingival sulcus 71 or 70 and remain exposed while the retrievable barrier membrane 1 is in place. At the appropriate time for membrane removal, the sutures or other devices holding the membrane in place are released. The free ends of the membrane retrieval cord 52 are grasped with a forceps and through gentle tension applied to the cord, the inferior border 40 of the membrane is retracted and the membrane rolls up upon itself moving occlusally. Ultimately, the entire membrane is pulled though the sulcus by maintaining tension on the cord.

FIG. 5 illustrates a second preferred embodiment of the invention. Seen from a top view looking toward the surface of the tooth 60, the superior border 31 of the semi-circular retrievable barrier membrane 2 is proximate to the neck 65 of the tooth 60. The loop 50 of retrieval cord extends from the superior border 31 of the barrier membrane 6. The intermediate portions of the cord 51 are affixed to the barrier membrane 6. The free ends 52 of the retrieval cord extend from the inferior border 41 of the barrier membrane 6.

FIG. 6 illustrates a third preferred embodiment of the invention. Here, the retrievable barrier membrane 3 lies between two teeth 60 and 61 in a top view looking at the teeth's biting or chewing surface. The superior borders 32 and 33 of the barrier membrane 7 are proximate to the necks of the teeth 60 and 61. In this third preferred embodiment, two separate retrieval cords are provided. The first retrieval cord comprising loop 50, intermediate portion 51 and free ends 52 is affixed to the first arm of the third embodiment with lateral inferior border 42. The second retrieval cord comprising loop 55, intermediate portion 56 and free ends 57 is affixed in an antisymmetric position to the first retrieval cord and affixed to the second arm of the third embodiment with lateral inferior border 43.

FIG. 7 depicts a sectional view of a plane through the tooth, roots, gum and underlying bony tissue and illustrates the invention as described in FIGS. 1–4. FIG. 7 depicts peripheral aspects of the bony tissue 90 and 91 in which the tooth 60 and its roots 65 are embedded. FIG. 7 further displays the gingival sulci 70 and 71 between the bony tissue 90 or 91 and the gum tissue 80 or 81.

FIG. 8 illustrates a perspective view of a fourth preferred embodiment of the invention with the retrievable barrier membrane 4 covering a deficit 100 in bony tissue 92. The longitudinal axis extending from first lateral border 70 to second lateral border 72 of barrier membrane 8 is parallel to the expanse of gum defined between locations 92 and 94. The retrieval cord with loop 50, intermediate portion 41 and free ends 52 is affixed perpendicularly to said longitudinal axis with said retrieval cord extending from longitudinal border 80 to longitudinal 82. FIG. 8 further depicts free ends 52 drawn through loop 50.

Figure 9:
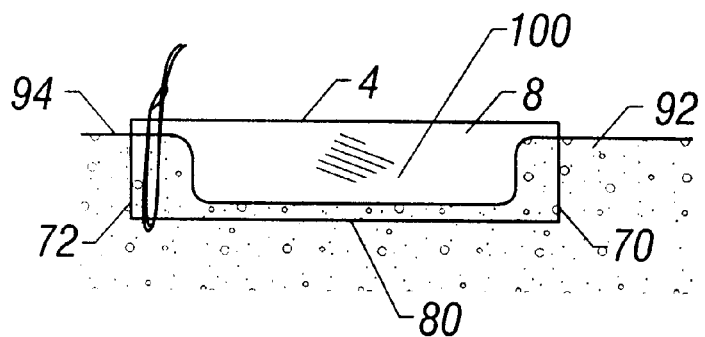
FIG. 9 is a side view illustrating a section seen through the gum of the same configuration of retrievable barrier membrane and tissue deficit shown in FIG. 8.

FIG. 9 is a section side view (from either a buccal or lingual aspect) seen through the gum (not shown) illustrating the bony deficit of FIG. 8 covered by the fourth preferred embodiment of the invention as previously described.

Figure 10:
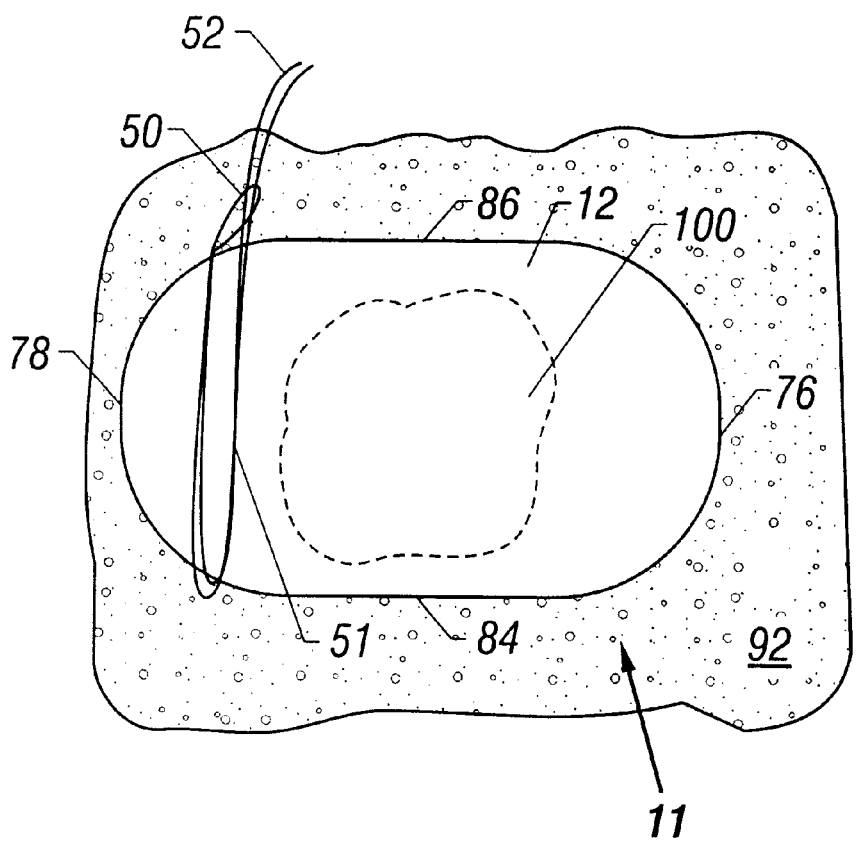
FIG. 10 is a schematic top view illustrating a fifth preferred embodiment of a device in accordance with the invention.

FIG. 10 illustrates a fifth preferred embodiment of the instant invention with a view from a superior aspect through the gum (not shown) toward a retrievable barrier membrane 11 with a retrieval cord with loop 50, intermediate portion 41 and free ends 52 affixed to barrier membrane 12 covering a bony deficit 100. The barrier membrane 12 has a longitudinal axis defined between first location 76 and second location 78. The intermediate portion 51 of the retrieval cord is affixed to barrier membrane 12 perpendicular to said longitudinal axis. The free ends 52 of the retrieval cord are drawn through loop 50. Use of the fifth preferred embodiment requires the free ends 52 of the retrieval cord to be further drawn through the gum to the surface. At the time of removal, a small incision may be made proximal to the free ends 52 and parallel to the longitudinal axis defined between first location 76 and second location 78. The free ends 52 may be grasped and retracted to remove the retrievable barrier 11.

The invention is preferably packaged in sterile kits including various configurations of barrier membranes with retrieval cords positions as previously described. The invention and its variations may be utilized in treating a variety of conditions. While contemplated for primary use in periodontal surgery, the device and method can be used to cover edentulous or tooth-bearing ridges in the effort to regenerate bone. The invention may further be utilized in attempts to regraft levels bone in oral surgery or in other orthopedic applications Those of ordinary skill in the art will see that the instant invention provides a superior method and mechanics for retracting and removing the membrane barrier without the need to perform extensive surgery. The instant invention enables membrane removal more efficiently by the attending clinician, may be performed under local anesthetic, reduces surgical trauma to the patient and, most importantly, reduces risk of injury to newly regenerated cells.

The foregoing is offered primarily for purposes of illustration. It will be readily apparent to those of ordinary skill in the art that the operating conditions, membrane barrier configurations, procedural steps and other parameters of the system described herein may be further modified or substituted in various ways without departing from the spirit and scope of the invention. Thus the invention is not limited by the preceding description but rather by the appended claims.

What is claimed is:

1. A retrievable mechanical barrier membrane comprising a cord affixed to said membrane barrier with the affixed portion of the cord running from the superior occlusal border of said membrane to the inferior periostal border; a loop formed by said cord extending from the superior border of said membrane; the free ends of said cord extending from the inferior border of said membrane, and said free ends insertable through said loop.

2. The method of removing a membrane barrier used to facilitate selective tissue regeneration of a tissue deficit comprising the steps of:
    inserting the free ends of retrieval cord through a loop formed by the retrieval cord a portion of which is affixed to said barrier membrane;
    grasping the free ends of said retrieval cord;
    pulling on said free ends causing the membrane barrier to roll upon itself moving occlusally.

3. The method of removing a barrier used to facilitate regeneration of a tissue deficit comprising the steps of:
    placing the barrier membrane proximately to a tissue deficit;
    inserting the free ends of a retrieval cord through a loop in the retrieval cord, said loop extending from the superior occlusal border of a barrier membrane;
    closing the incision with tissue covering the barrier membrane and guiding the free ends of the retrieval cord through the proximate gingival sulcus;
    grasping the free ends of a retrieval cord extending from the inferior periostal border of a barrier membrane;
    pulling on said free ends of said retrieval cord causing the membrane barrier to roll upon itself moving occlusally.

4. The method of removing a membrane barrier used to facilitate regeneration of a tissue deficit comprising the steps of:
    inserting the first set of free ends of a first retrieval cord through a loop in said first retrieval cord, said loop extending from the first superior border of a barrier membrane;
    inserting the second set of free ends of a second retrieval cord through a loop in said second retrieval cord, said loop extending from the second superior border of a barrier membrane;
    grasping the first set of free ends of a first retrieval cord extending from a first inferior periostal border of a barrier membrane;
    pulling on said first set of free ends of said first retrieval cord causing a portion of the membrane barrier to roll upon itself moving occlusally;
    grasping the second set of free ends of a second retrieval cord extending from a second inferior border of a barrier membrane;
    pulling on said second set of free ends of said second retrieval cord causing the remaining portion of the membrane barrier to roll upon itself moving occlusally.

* * * * *